US007828720B2

(12) United States Patent
Miller et al.

(10) Patent No.: US 7,828,720 B2
(45) Date of Patent: Nov. 9, 2010

(54) SURGICAL ADAPTER (75) Inventors: Michael E. Miller, Trafalgar, IN (US);
Joseph L. Mark, Indianapolis, IN (US)

(73) Assignee: Nico Corporation, Indianapolis, IN (US)

( * ) Notice: Subject to any disclaimer, the term of this patent is extended or adjusted under 35 U.S.C. 154(b) by 1163 days.

(21) Appl. No.: 11/110,519

(22) Filed: Apr. 20, 2005

(65) Prior Publication Data

US 2006/0241343 A1    Oct. 26, 2006

(51) Int. Cl.
*A61B 1/00* (2006.01)
(52) U.S. Cl. .................. 600/104; 600/102; 600/106; 600/117
(58) Field of Classification Search ............... 600/102, 600/104, 106, 117, 154
See application file for complete search history.

(56) References Cited

U.S. PATENT DOCUMENTS

| 4,142,517 | A |   | 3/1979  | Stavropoulos |            |
|-----------|---|---|---------|--------------|------------|
| 4,421,106 | A | * | 12/1983 | Uehara       | 600/106    |
| 4,586,491 | A | * | 5/1986  | Carpenter    | 600/113    |
| 4,696,544 | A | * | 9/1987  | Costella     | 385/118    |
| 5,431,645 | A | * | 7/1995  | Smith et al. | 606/1      |
| 5,607,386 | A | * | 3/1997  | Flam         | 600/120    |
| 5,669,915 | A |   | 9/1997  | Caspar et al.|            |
| 6,520,954 | B2| * | 2/2003  | Ouchi        | 606/1      |
| 6,679,833 | B2| * | 1/2004  | Smith et al. | 600/114    |
| 6,726,675 | B1| * | 4/2004  | Beyar        | 604/510    |
| 7,241,263 | B2| * | 7/2007  | Boulais      | 600/137    |
| 7,347,829 | B2| * | 3/2008  | Mark et al.  | 600/567    |
| 2004/0077938 | A1 |  | 4/2004 | Mark et al. |             |
| 2004/0199049 | A1 | * | 10/2004 | Parasher et al. | 600/106 |
| 2005/0148820 | A1 | * | 7/2005 | Carrillo    | 600/154    |

FOREIGN PATENT DOCUMENTS

EP      1 290 971 A2     3/2003

OTHER PUBLICATIONS

PCT International Search Report PCT/IB/2006/051063 dated Nov. 15, 2006.

* cited by examiner

*Primary Examiner*—Matthew J Kasztejna
(74) *Attorney, Agent, or Firm*—Rader, Fishman & Grauer, PLLC (57) ABSTRACT

A surgical system is provided that includes a device body that has a working channel providing a pathway for an instrument, an extension adjuster engaged with the device body, the extension adjuster also including a stop. The stop is disposed a predetermined distance from the working channel such that the stop and the distal end of the working channel cooperate to define an effective working channel length. The instrument may be inserted through the working channel and protrude outwardly from the distal end of the working channel. The extent of the protrusion is limited by the effective working channel length whereby the stop prevents further insertion of the instrument.

18 Claims, 9 Drawing Sheets

SURGICAL ADAPTER

BACKGROUND OF THE INVENTION

1. Field of the Invention

The present invention relates generally to devices adapted for introducing a surgical device into the body of a patient and, more particularly, to a device for controllably positioning a medical device within the patient.

2. Description of the Related Art

Endoscopic surgery allows for surgery to be performed while reducing damage to the surrounding tissue as compared to standard surgical procedures. An endoscope which may include at least one working channel, allows the insertion and deployment of various medical devices to the surgical site. The endoscope also provides visualization of the surgical site during the procedure.

Once the desired position of the surgical site is reached, a surgical instrument may be inserted through the working channel and protrude from the distal end of the working channel at the visualized surgical site. In some cases a bladed cutter is introduced to excise tissue from the surgical site. Such a bladed cutter generally requires connection to a handpiece that provides rotary or reciprocative motion to the cutting portion of the instrument. When the cutting operation is enabled, tissue is generally drawn through the mouth of the cutting instrument by suction and then is severed by the cutter. The suction also removes the dislodged tissue from the patient.

Unfortunately, during the procedure the handpiece must be constantly manipulated by the surgeon to control the extension of the instrument beyond the working channel of the endoscope, as well as the vertical/horizontal support of the scope portion. The extension depth from the endoscope working channel and the vertical/horizontal support of the scope portion must be constantly controlled using the surgeon's hand hand-eye coordination. This constant control of the instrument causes fatigue in the surgeon and makes it difficult to precisely position during the procedure.

Further, during an endoscopic procedure it is necessary to adjust the depth of the medical device within the patient in order to precisely target a lesion for removal. To this end, the cutting element must be accurately positioned adjacent the lesion. While conventional use of endoscopes systems allow for insertion of a surgical device through the working channel, they do not provide for adjustability and maintenance of depth registration with the surgical site by maintaining the protrusion of the surgical instrument from the distal end of the working channel. Additionally, conventional systems to not allow for the removal and reinsertion of the surgical device from the working channel while maintaining the original registration.

Accordingly, a surgical adapter is needed that precisely controls the protrusion of the medical instrument from the working channel without requiring constant attention to fine hand-eye coordination. Further, a need exists for a surgical adapter that facilitates adjustable and fixed positioning of the device within the patient, removal of the device from the working channel, and reinsertion of the device through the working channel to the same fixed position. Finally, a system that may provide additional safeguards against inadvertent tissue damage is also desired. Such a system would allow removal of the device from the working channel so that other devices or therapeutics may be introduced into the patient, as needed. The original device may then be reinserted into the working channel and reintroduced at precisely the same pre-removal orientation.

SUMMARY OF THE INVENTION

A surgical system is provided that includes a device body that has a working channel providing a pathway for an instrument and an extension adjuster that is engaged with the device body. The extension adjuster also includes a stop. The stop is disposed a predetermined distance from the working channel such that the stop and a distal end of the working channel cooperate to define an effective working channel length. The instrument may be inserted through the working channel and protrude outwardly form the distal end of the working channel. The extent of the protrusion is limited by the effective working channel length whereby the stop prevents further insertion of the instrument.

The surgical system may also include a handpiece that is engaged with the instrument. In such a case, when the handpiece engages the stop, the handpiece and the instrument may no longer move distally towards the working channel and thus the protrusion of the instrument is limited. The surgical system may also include a guide system that stabilizes the instrument or handpiece and provides registration of the handpiece or instrument to the adapter. Using the guide system, the surgical system allows for selective removal of the instrument from the working channel and later reinsertion of the instrument while maintaining the same pre-removal depth registration and axial registration.

Among other features, the surgical system provides the ability to adjustably limit protrusion of the instrument from the working channel while allowing for the removal and reinsertion of the instrument and maintaining depth and axial registration. With the instrument removed, other procedures may be performed or therapeutics may be administered to the surgical site. The present invention further allows for reinsertion of the instrument with the prior registration maintained.

BRIEF DESCRIPTION OF THE DRAWINGS

The features and inventive aspects of the present invention will become more apparent upon reading the following detailed description, claim s, and drawings, of which the following is a brief description:

DETAILED DESCRIPTION

Referring now to the drawings, preferred embodiments of the present invention are shown in detail. Although the drawings represent embodiments of the present invention, the drawings are not necessarily to scale and certain features may be exaggerated to better illustrate and explain the present invention. The embodiments set forth herein are not intended to be exhaustive or otherwise limit the invention to the precise forms disclosed in the following detailed description.

Figures 1A, 1B:
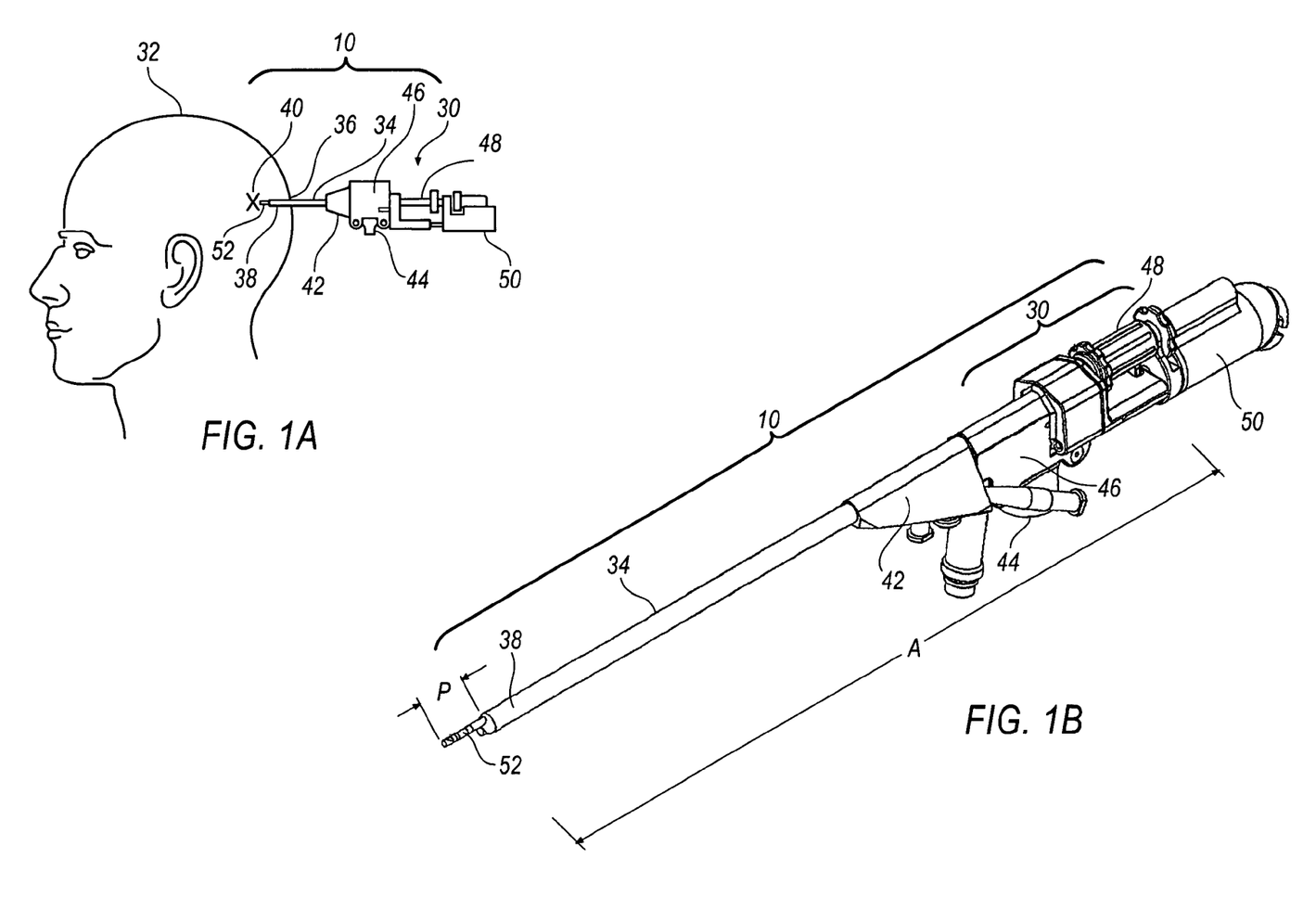
FIG. 1A is a simplified side elevation view of an embodiment of a surgical system of the present invention.
FIG. 1B is a perspective view of an embodiment of a surgical system of the present invention.

Referring to FIG. 1A, there is shown a simplified side elevation view of an embodiment of a surgical system 10 of the present invention. Surgical system 10 includes a surgical adapter 30, an endoscope 44, an endoscope adapter 46, an extension adjuster 48, a handpiece 50, an introducer body 42, a working channel 34, and a blade 52. Working channel 34 is a narrow passage that allows access to a surgical site 40.

Typically, working channel 34 pierces a patient 32 at an incision site 36 and a distal end 38 is pushed through surrounding tissue until the appropriate depth is reached. Blade 52 is then inserted through working channel 34 for access to surgical site 40. Endoscope 44 may also be used to visualize surgical site 40 and may provide working channel 34.

Once distal end 38 of working channel 34 is in position, working channel 34 may be used for a variety of medical procedures, such as introducing surgical instruments, delivering medicines, delivering markers, irrigating, and removing tissues and fluids. Handpiece 50 may be attached to blade 52 for driving the cutting instrument or otherwise providing vacuum assistance. Extension adjuster 48 may be used to extend the distance from distal end 38 to handpiece 50, or the proximal end (not shown) of blade 52.

FIG. 1B illustrates a perspective view of an embodiment of surgical system 10 of the present invention. Surgical system 10 includes working channel 34, introducer body 42, endoscope 44, endoscope adapter 46, extension adjuster 48, and handpiece 50. Specifically, surgical adapter 30 consists of endoscope adapter 46 and extension adjuster 48. The other components are illustrative of a typical, but non-exclusive, use for surgical adapter 30. Cutting instrument blade 52 runs the length of the system from handpiece 50 through extension adjuster 48 and through working channel 34 to distal end 38 of working channel 34. Working channel 34 may also extend into extension adjuster 48 if so desired. Blade 52 is preferably removably attached to, and driven by, handpiece 50.

The present invention provides for controlled and repeatable protrusion P of blade 52 from distal end 38. Protrusion P is controlled by an effective working channel distance A that is measured from the proximal end of extension adjuster 48 to distal end 38. Extension adjuster 48 may be adjusted (explained in more detail later) to set effective working channel distance A to a predetermined distance. Assuming that blade 52 is longer than effective working channel distance A, placing blade 52 into working channel 34 and pushing distally until handpiece 50 engages extension adjuster 48 will cause blade 52 to protrude a fixed distance beyond distal end 38. Thus, by setting effective working channel distance A the invention allows for multiple extractions and insertions of blade 52 through working channel 34 with a repeatable protrusion P so long as handpiece 50 is moved fully towards extension adjuster 48 with each insertion.

A surgeon may set protrusion a distance P of blade 52 using extension adjuster 48 and leave the instrument in the desired position without holding handpiece 50. Thus, extension adjuster 48 allows for precise control of the surgical instrument without requiring the surgeon's attention or reliance on hand-eye coordination to manually maintain positioning. The surgeon may also adjust protrusion distance P during surgery by resetting extension adjuster 48 to maintain a new effective working channel distance A.

Figure 2:
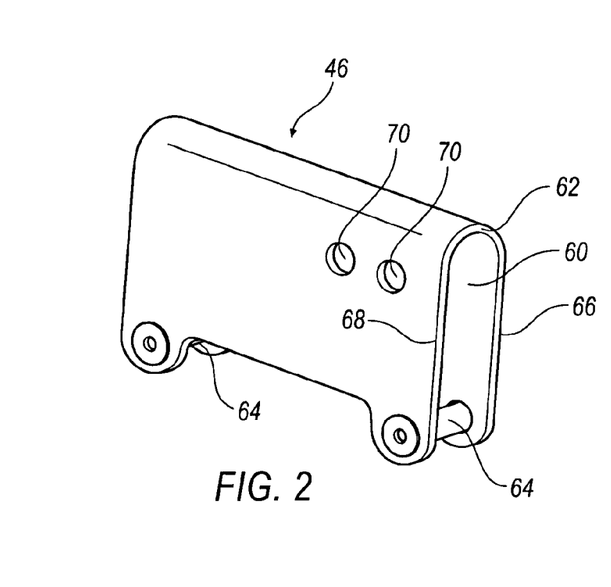
FIG. 2 is a perspective view of an endoscope adapter for use with the surgical system of FIG. 1B.

Referring to FIG. 2, there is shown a perspective view of an endoscope adapter 46 for use with surgical system 10. Endoscope adapter 46 includes an adapter body 62, clamping screws 64, walls 66, 68, and attachment points 70. In the present embodiment, endoscope adapter 46 is configured to accept endoscope 44 within a cavity 60. However, the present invention is not limited to accepting endoscopes within cavity 60 and may be configured to otherwise attach to an endoscope using bolts, clamps, or other methods suitable for the surgical environment. Additionally, endoscopic adapter 46 may engage with other medical devices entirely and need not be adapted solely for use with endoscope 44. Clamping screws 64 are used to force walls 66, 68 of adapter body 62 together and against endoscope 44 (see FIG. 1B). Endoscope adapter 46 may also include attachment points 70 that facilitate attachment of extension adjuster 48 (see FIG. 1B).

Figure 3:
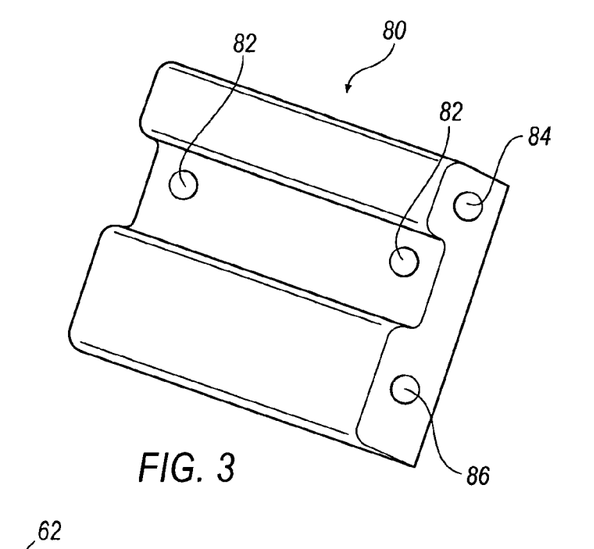
FIG. 3 is a perspective view of an extension adapter for use with the surgical system of FIG. 1B.

FIG. 3 illustrates a perspective view of an extension mount 80 for use with surgical system 10. Extension mount 80 is configured to mate with both endoscope adapter 46 (see FIG. 2) and extension adjuster 48 (see FIG. 1B). Fastening holes 82 align and mate with attachment points 70 of endoscope adapter 46 (see FIG. 2). Extension mount 80 also includes an adjuster receiver 84 used to engage extension adjuster 48. Extension mount 80 further comprises a guide passage 86 as part of a guide system (explained in detail later) that aligns blade 52 with working channel 34.

Figure 4:
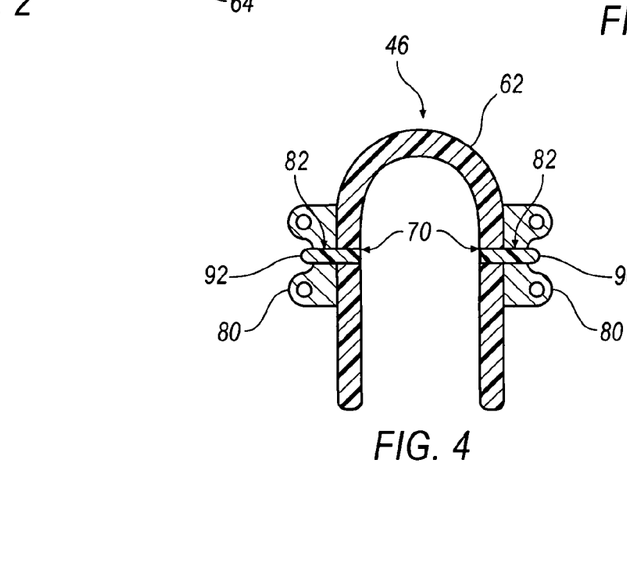
FIG. 4 is a cross-sectional view of the endoscope adapter of FIG. 2 with attached extension mounts of FIG. 3 for use with the surgical system of FIG. 1B.

FIG. 4 illustrates a cross-sectional view of endoscope adapter 46 of FIG. 2 with attached extension mounts 80 of FIG. 3 for use with surgical system 10. Two extension mounts 80 are attached to adapter body 62 on each wall 66, 68 using screws 90, 92. Securing extension mounts 80 to adapter body 62, screws 90, 92 are configured to pass through fastening holes 82 of extension mount 80, and mate with attachment points 70. Although the present embodiment illustrates the use of two screws 90, 92 for each extension mount 80, the invention is not limited to such an attachment method. Extension mount 80 may be attached to adapter body 62 by a single screw 90, multiple screws 90, 92, or using attachment methods such as welding or gluing. Alternately, extension mount 80 may be integrally formed with endoscope adapter 46 so as to produce a unitary structure.

Figure 5:
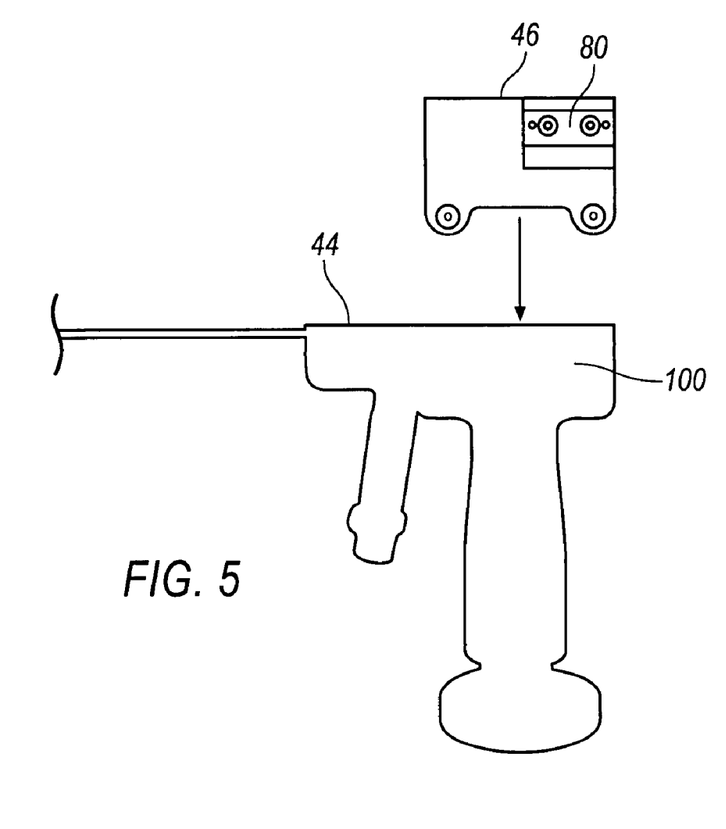
FIG. 5 is a simplified side perspective view of the endoscope adapter of FIG. 3 being installed onto an endoscope.

FIG. 5 illustrates a simplified side perspective view of endoscope adapter 46 of FIG. 3 being installed onto endoscope 44. Endoscope adapter 46 is positioned relative to an endoscope body 100 and then moved toward endoscope body 100 such that endoscope body 100 is received by endoscope adapter 46 within cavity 60 (see FIG. 2).

Figure 6:
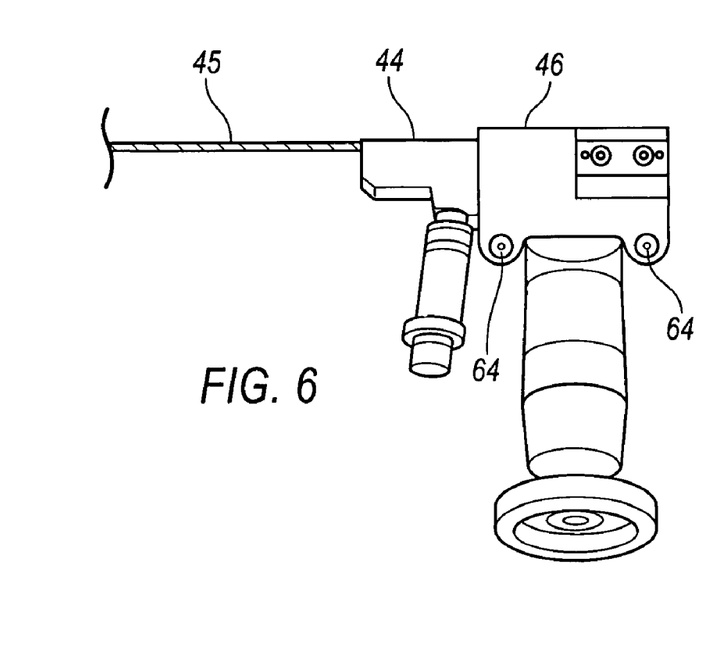
FIG. 6 is a simplified side perspective view of the endoscope adapter of FIG. 3 installed on an endoscope.

FIG. 6 illustrates a simplified side perspective view of endoscope adapter 46 of FIG. 3 installed on endoscope 44. After endoscope 44 is fully received by endoscope adapter 46, clamping screws 64 may be attached such that walls 66, 68 (see FIG. 2) of endoscope adapter 46 press against endoscope 44 securing endoscope adapter 46 and endoscope 44 together.

Figure 7:
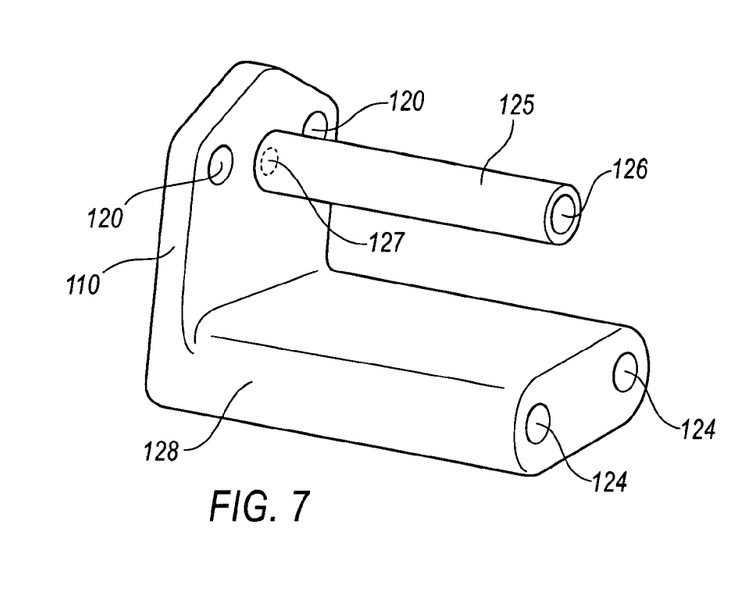
FIG. 7 is a perspective view of an extension bolt for use with the extension adjuster of FIG. 1B.

FIG. 7 illustrates a perspective view of an extension bolt 125 for use with extension adjuster 48 of FIG. 1B. Extension bolt 125 is defined by a distal end and a proximal end and attached to a mounting bracket 110 such that the proximal end extends in a proximal direction from the mounting bracket. A passage extends through extension bolt 125 from a first opening 126 to a second opening 127. Both first opening 126 and second opening 127 are coaxial with the working channel opening (not shown) and work cooperatively with an outer opening 118 (see FIG. 8) to provide access working channel 34. The passage created between openings 118, 126, 127 provides blade 52 access to working channel 34 of endoscope 44. In the present embodiment, second opening 127 is adjacent to the working channel opening of the endoscope (not shown). However, alternate embodiments may provide the working channel opening (not shown) some fixed distance from second opening 127. A lower portion 128 of extension adjuster 48 also includes guide passages 124 for use with guide rails 202 (see FIG. 12) to be explained in further detail below. In use, an extension nut 112 (see FIG. 8) threadingly engages extension bolt 125. A threaded outer portion 150 of extension bolt 125 accepts a threaded inner portion 144 of extension nut 112 (explained later in detail, see FIGS. 9-10C).

Figure 8:
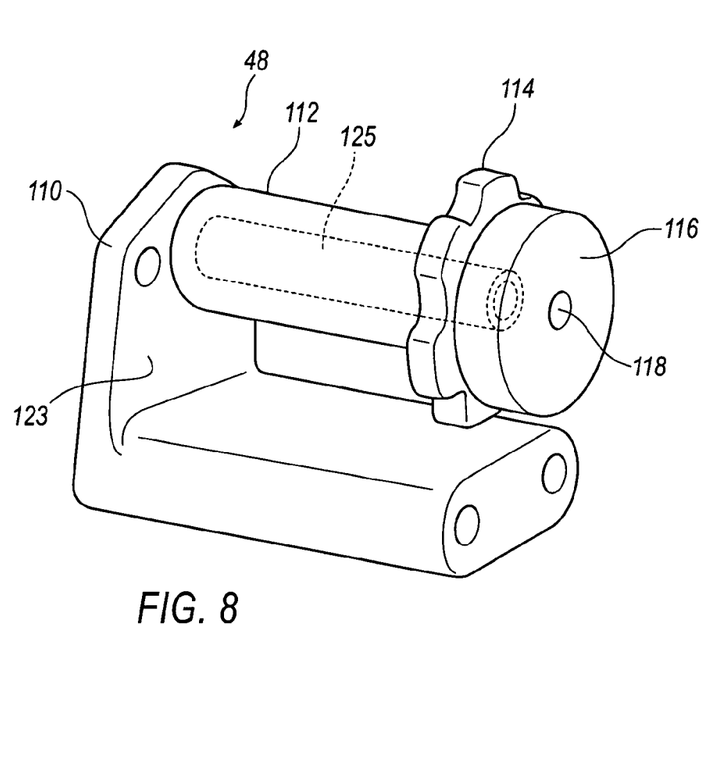
FIG. 8 is a perspective view of an extension nut installed on the extension bolt of FIG. 7, creating an extension adjuster for use with the surgical system of FIG. 1B.

FIG. 8 illustrates a perspective view of extension nut 112 installed on extension bolt 125 of FIG. 7, creating extension adjuster 48 for use with surgical system 10. Extension adjuster 48 includes mounting bracket 110, extension nut 112, extension bolt 125, a thumbwheel 114, an abutting surface 116, and outer opening 118. Mounting bracket 110 is used to attach extension adjuster 48 to surgical system 10. Mounting bracket 110 includes a wall member that, in the embodiment shown in FIGS. 7-8, includes an upwardly extending wall and a lower portion 128. The wall member is defined by a distal surface and an opposing proximal surface, also referred to as an interior surface 123 (best seen in FIG. 10C). Outer opening 118 is mounted coaxial with the working channel opening (not shown) and provides access for blade 52, or other surgical instrument, to working channel 34. Thumbwheel 114 is used by the surgeon to adjust the extension or protrusion distance P of blade 52 beyond distal end 38 of working channel 34 (see FIG. 1B). Abutting surface 116 is configured to interface with handpiece 50 and prevent handpiece 50 from moving any farther than abutting surface 116 toward the working channel opening (not shown). As illustrated, extension nut 112 is fully closed as it touches an interior surface 123 of mounting bracket 110.

When assembled, mounting bracket 110 aligns and mates with extension mount 80. Each mounting hole 120 aligns with each complementary adjuster receiver 84 of extension mounts 80. Screws may then be inserted through mounting holes 120 and received by adjuster receivers 84, thus fixingly attaching mounting bracket 110 to endoscope adapter 46 through extension mounts 80. Lower portion 128 further comprises guide passages 124 which are open channels that slidingly receive guide rails 202 (see FIG. 12).

Figure 9:
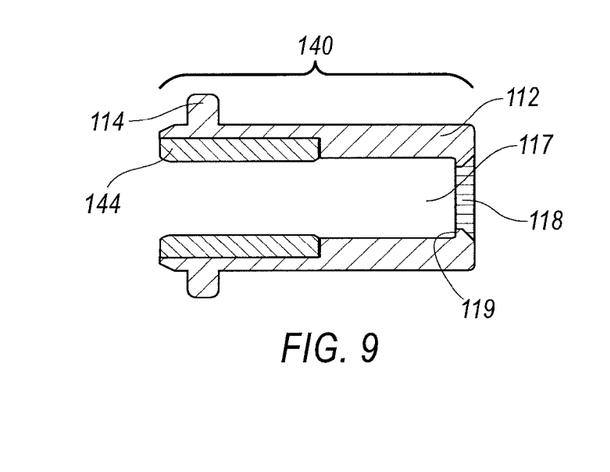
FIG. 9 is a cross-sectional view of the extension nut for use with the extension adjuster of FIG. 8.

FIG. 9 illustrates a cross-sectional view of extension nut 112 for use with extension adjuster 48 of FIG. 8. A thumbwheel adjuster 140 includes extension nut 112, thumbwheel 114, outer opening 118 and threaded inner portion 144. Extension nut 112 is defined by a proximal end and a distal end. Extension nut 112 further includes an interior chamber 117 that is in communication with outer opening 118 that is formed through the proximal end of the extension nut 112. As may be seen, interior chamber 117 is sized so as to be larger than outer opening 118, forming a land member 119 surrounding outer opening 118 on an interior surface of extension nut 112. Threaded inner portion 144 extends from the distal end of extension nut 112, and is disposed along at least a portion of an inner wall that defines interior chamber 117. Thumbwheel 114 is used by the surgeon to set protrusion distance P blade 52 will extend beyond distal end 38 of working channel 34 (see FIG. 1B). Threaded inner portion 144 interfaces with threaded outer portion 150 of extension bolt 125 (explained below). Outer opening 118 is coaxial with the working channel opening (not shown) and provides blade 52 access to working channel 34.

Figure 10A:
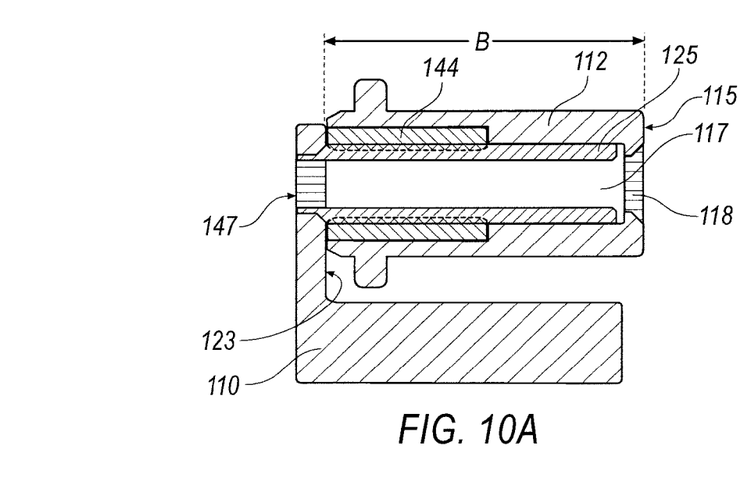
FIG. 10A is a cross-sectional view of the extension adjuster in a closed position in accordance with the present invention.

FIG. 10A illustrates a cross-sectional view of extension adjuster 48 in a closed position in accordance with the present invention. A first distance B may be measured by the distance between an abutting surface 115 and interior surface 123 of mounting bracket 110. In this embodiment, abutting surface 115 is also the proximal end of extension nut 112. First distance B is also parallel to working channel 34 and thus lengthens effective working channel distance A (see FIG. 1B). As first distance B increases, protrusion distance P of blade 52 is reduced. As illustrated, thumbwheel 114 (see FIGS. 7, 9) may be located toward the distal or proximal end of extension nut 112.

Figure 10B:
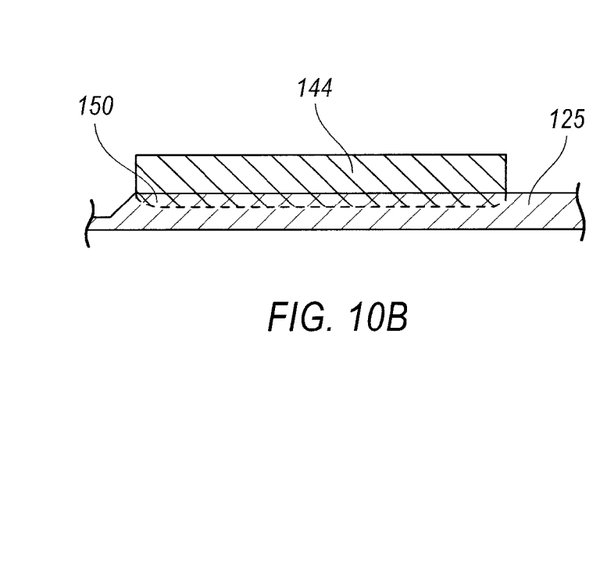
FIG. 10B is a cross-sectional view of the interface of the extension nut of FIG. 8 and the extension bolt of FIG. 7 of the extension adjuster of FIG. 10A in accordance with the present invention.

FIG. 10B illustrates a cross-sectional view of the interface of extension nut 112 and extension bolt 125 of extension adjuster 48. Extension bolt 125 includes threaded outer portion 150 that contacts threaded inner portion 144 of extension nut 112. The two portions threadingly interface to provide proximal and distal adjustment of extension nut 112 relative to extension bolt 125 when extension nut 112 is turned. The present embodiment uses, but is not limited to, a right-hand thread arrangement between threaded inner portion 144 and extension bolt 125. Due to the right-hand thread interface of threaded inner portion 144 and extension bolt 125, clockwise movement of thumbwheel adjuster 140 will reduce first distance B, thus extending blade 52 farther beyond distal end 38. Consequently, counter-clockwise movement of thumbwheel adjuster 140 will increase first distance B, thus retracting blade 52 within distal end 38.

Figure 10C:
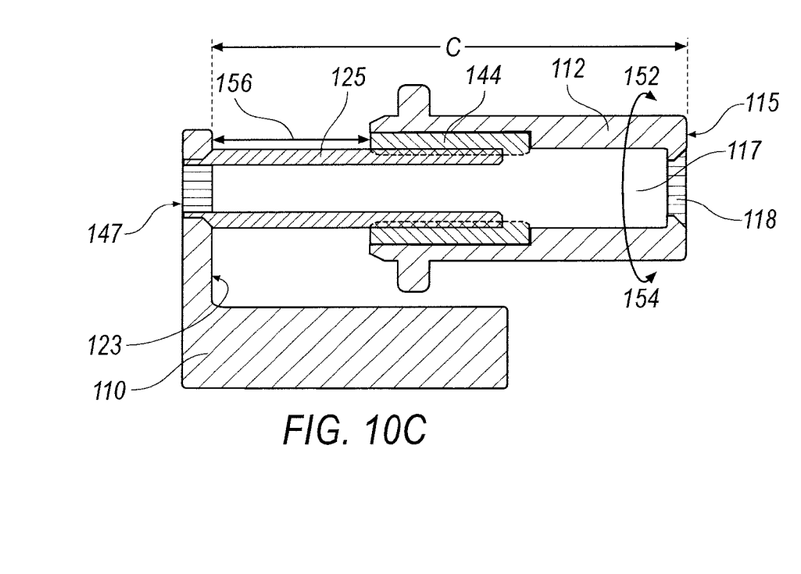
FIG. 10C is a cross-sectional view of an extension adjuster in an open position in accordance with the present invention.

FIG. 10C illustrates a cross-sectional view of extension adjuster 48 in an open position. As described in FIG. 10B, extension nut 112 threadingly engages with extension bolt 125 such that extension nut 112 is received within interior chamber 117 of extension bolt 125 and the passage of the extension bolt 125 aligns with outer opening 118. Thus, extension adjuster 48 is opened or closed by turning extension nut 112. Here, extension adjuster 48 is opened to a second distance C by turning extension nut 112 counter clockwise. In this case, extension nut 112 constitutes a stop. Second distance C may be measured by the distance between abutting surface 115 and interior surface 123 of mounting bracket 110, the same measurement as first distance B. In this case, second distance C is greater than first distance B because extension adjuster 48 has been opened. Alternately, second distance C may be reduced by closing extension adjuster 48.

Figure 11:
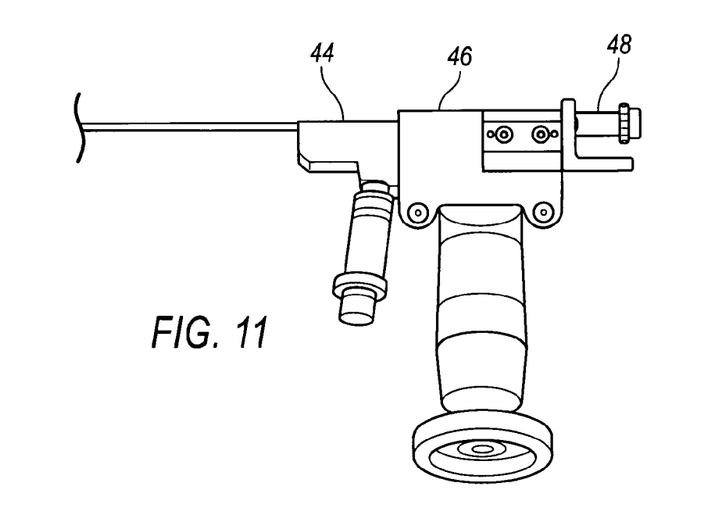
FIG. 11 is a side perspective view of the extension adjuster installed with the endoscope adapter of FIG. 4.

FIG. 11 illustrates a side perspective view of extension adjuster 48 installed with endoscope adapter 46. When installed, endoscope adapter 46 and extension adjuster 48 are rigidly engaged with endoscope 44. Instrument passages and openings 118, 126, 127, 147 (see FIGS. 7-10) provide for the normal use of surgical instruments, or blades 52, with surgical system 10.

Figure 12:
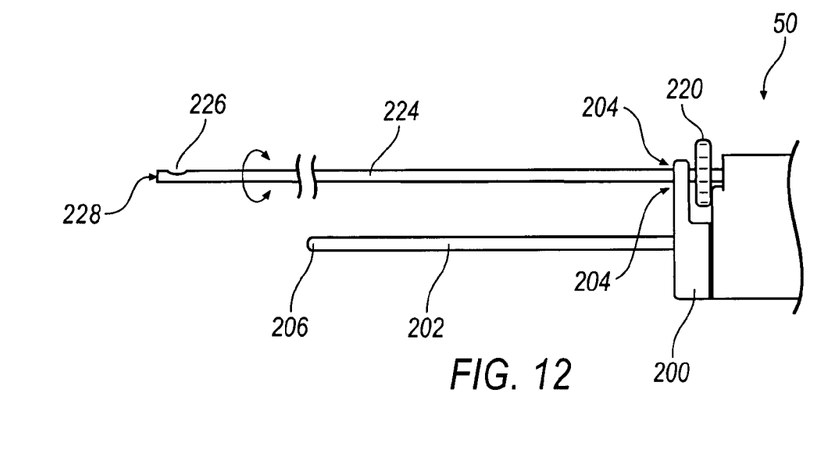
FIG. 12 illustrates a side elevation view of the receiving end of the handpiece of FIG. 1B for use with the endoscope adapter.

FIG. 12 illustrates a side elevation view of the receiving end of handpiece 50 for use with endoscope adapter 46. Handpiece 50 is configured to mate with extension adjuster 48 for surgical use. A handpiece body 200 includes guide rails 202 and a stop face 204. Stop face 204 surrounds an outer cannula 224 of blade 52. Guide rails 202 are used in conjunction with guide passages 86, 122, 124 (see FIGS. 3, 8) to generally stabilize handpiece 50 and to allow for the insertion of a surgical instrument, or blade 52, while maintaining registration with instrument passages and openings 118, 126, 127, 147. The registration and stabilization avoids damage to the instrument due to misalignment, bending, excessive force on handpiece 50, endoscope 44, endoscope adapter 46, or extension adjuster 48.

In practice, guide tip 206 of guide rail 202 is inserted into guide passage 124 of mounting bracket 110 or lower portion 128 (see FIG. 8). With further insertion, guide rail 202 will completely pass through guide passage 124 and enter similarly aligned guide passage 86. Guide rail 202 may freely and completely pass through extension mount 80 until stop face 204 contacts abutting surface 115, 116 (see FIGS. 7, 10A).

Further illustrated is an axial positioner 220 that may be used to rotate outer cannula 224 and a tissue receiving opening 226. Using both axial positioner 220 and extension adjuster 48, protrusion distance P and the axial registration of blade 52 are adjustable. Depth registration, or protrusion distance P, is maintained with the interface of abutting surface 115, 116 and stop face 204 inhibiting movement of handpiece 50 towards working channel 34 of endoscope 44. Axial registration is preserved by axial positioner 220. Since handpiece 50 and blade 52 are removable from surgical system 10, protrusion distance P and axial registration are preserved and can be precisely re-located by reinserting blade 52 until handpiece 50 engages abutting surface 115, 116. When handpiece 50 and blade 52 are returned to the system, both the protrusion and axial positions are maintained so long as extension adjuster 48 and axial positioner 220 are left unchanged. Registration of handpiece 50 to surgical adapter 30 is accomplished by working channel 34 registration with blade 52, and a guide system comprising guide passages 124 and guide rails 202 (see FIGS. 7, 12).

Figure 13A:
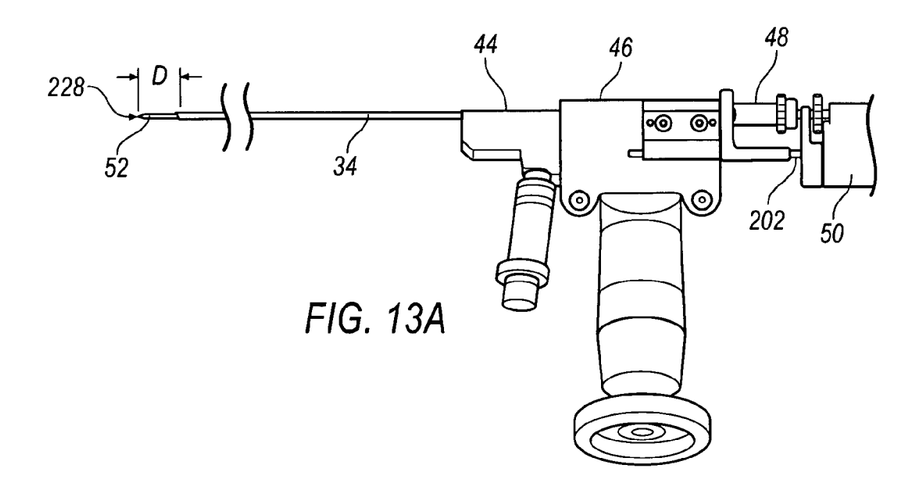
FIG. 13A is a side elevation view of the surgical system, wherein the extension adjuster is in a substantially closed position.

FIG. 13A illustrates a side elevation view of surgical system 10, wherein extension adjuster 48 is in a substantially closed position. Guide rail 202 of handpiece 50 freely slides within guide passages 86, 124 (see FIGS. 3, 8). Blade 52 is selectively attached to handpiece 50 and moves freely through opening 118, 126, 127, 147 (see FIGS. 7-10) and working channel 34 (see FIG. 1B). A third distance D of blade 52 is measured from distal end 38 of working channel 34 to a blade tip 228 of blade 52. When extension adjuster 48 is in the closed position, handpiece 50 is close to the working channel opening (not shown). Therefore, blade 52 protrudes third distance D, which is the maximum amount.

Figure 13B:
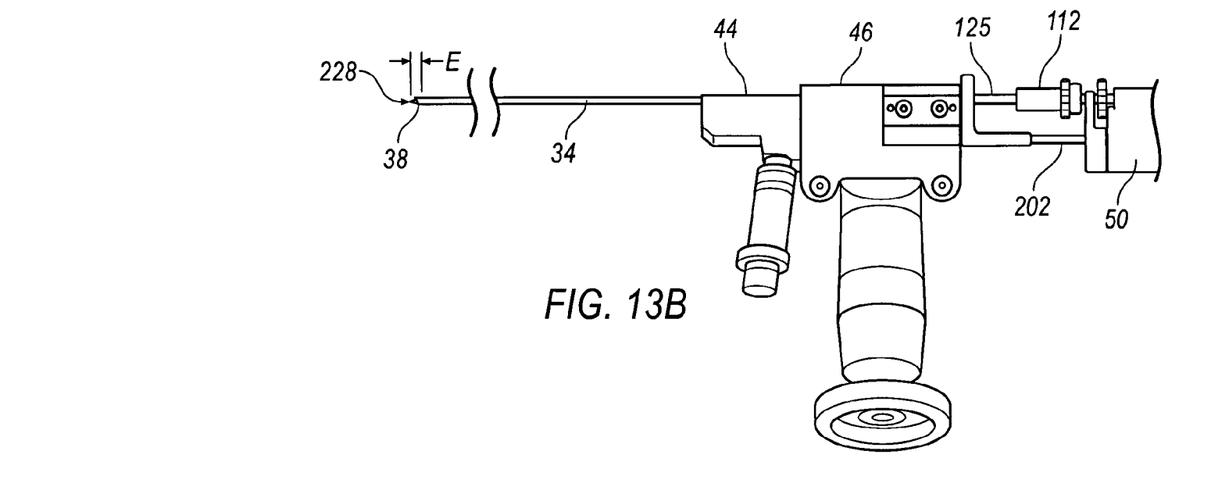
FIG. 13B is a side elevation view of the surgical system, wherein the extension adjuster is in a substantially open position.

FIG. 13B illustrates a side elevation view of surgical system 10, wherein extension adjuster 48 is in a substantially open position. Extension adjuster 48 is in the open position and handpiece 50 is farther away from working channel 34 (see FIG. 13A to compare). Consequently, blade 52 protrudes a fourth distance E, which is less than third distance D when extension adjuster 48 is in the closed position (illustrated in FIG. 13A).

In general, extension adjuster 48 controls protrusion of blade 52 by blocking movement of handpiece 50 toward working channel 34. With blade 52 connected to handpiece 50, blade 52 cannot protrude beyond a maximum predetermined distance because handpiece 50 is blocked by abutting surface 115, 116. When abutting surface 115, 116 is moved proximally toward handpiece 50, blade 52 will protrude less than if abutting surface 115, 116 is moved distally toward working channel 34.

Figure 14:
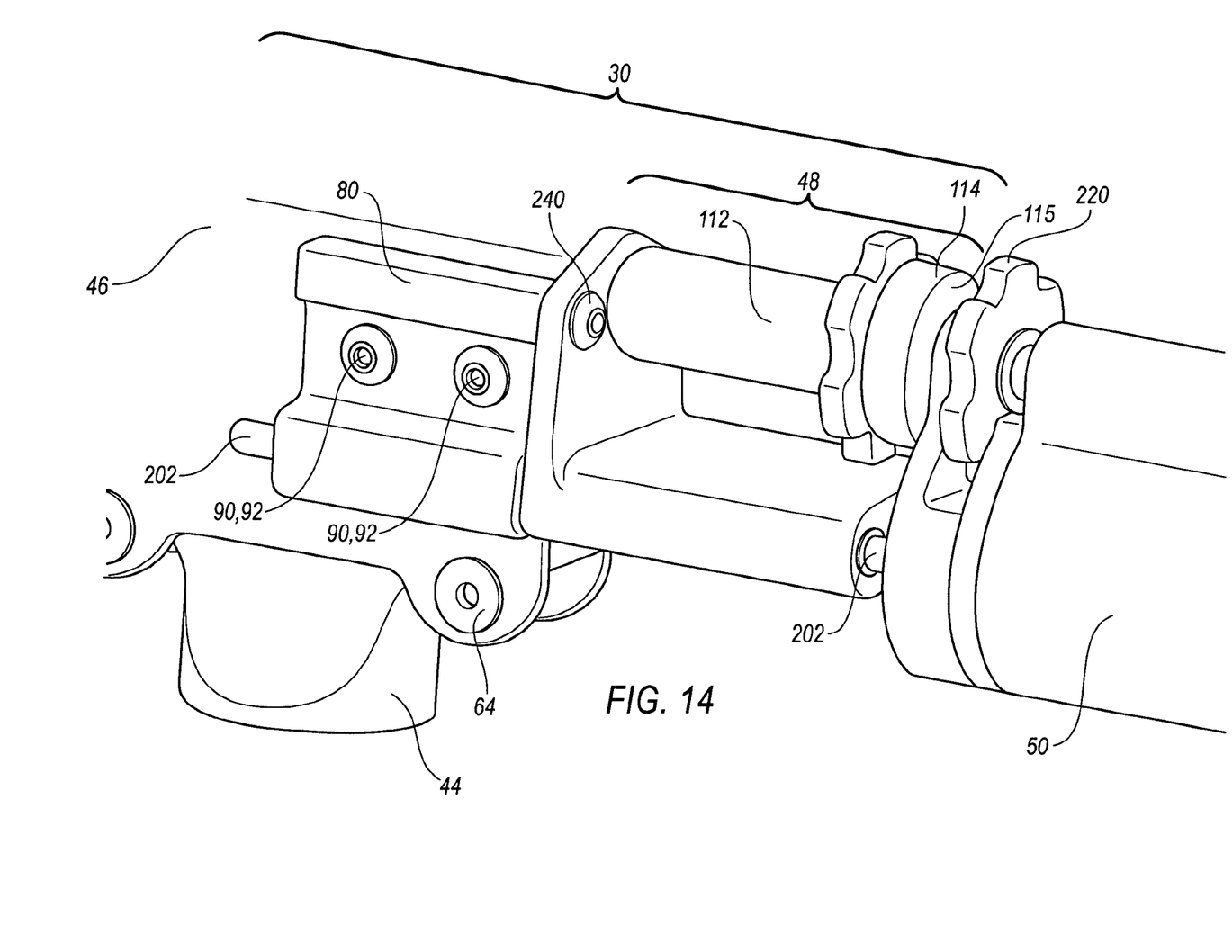
FIG. 14 is an enlarged perspective view of a portion of the surgical system with the extension adjuster and endoscope adapter incorporated therein.

FIG. 14 illustrates an enlarged perspective view of a portion of surgical system 10 with extension adjuster 48 and endoscope adapter 46 incorporated therein. In this exemplary embodiment, endoscope 44 is received within cavity 60 of endoscope adapter 46 and is secured with clamping screws 64. Extension mount 80 is secured to endoscope adapter 46 by screws 90, 92. A similar extension mount (not shown) is mirrored on the opposite side of endoscope adapter 46. Extension adjuster 48 is attached to extension mount 80 by screws 240. Alternately, extension adjuster 48 may be attached using locking pins or may be an integrated part of endoscope adapter 46. Extension adjuster 48 includes extension nut 112 and adjustment thumbwheel 114 for adjusting the maximum protrusion distance of the surgical instrument from working channel 34 (see FIG. 1B).

Handpiece 50 engages surgical adapter 30 with guide rail 202 sliding freely within guide passages 86, 122, 124 (see FIGS. 3 and 8). Abutting surface 115 engages handpiece 50 and thus limits the depth of blade 52 extending from distal end 38 of working channel 34 (see FIG. 1B).

Figure 15A:
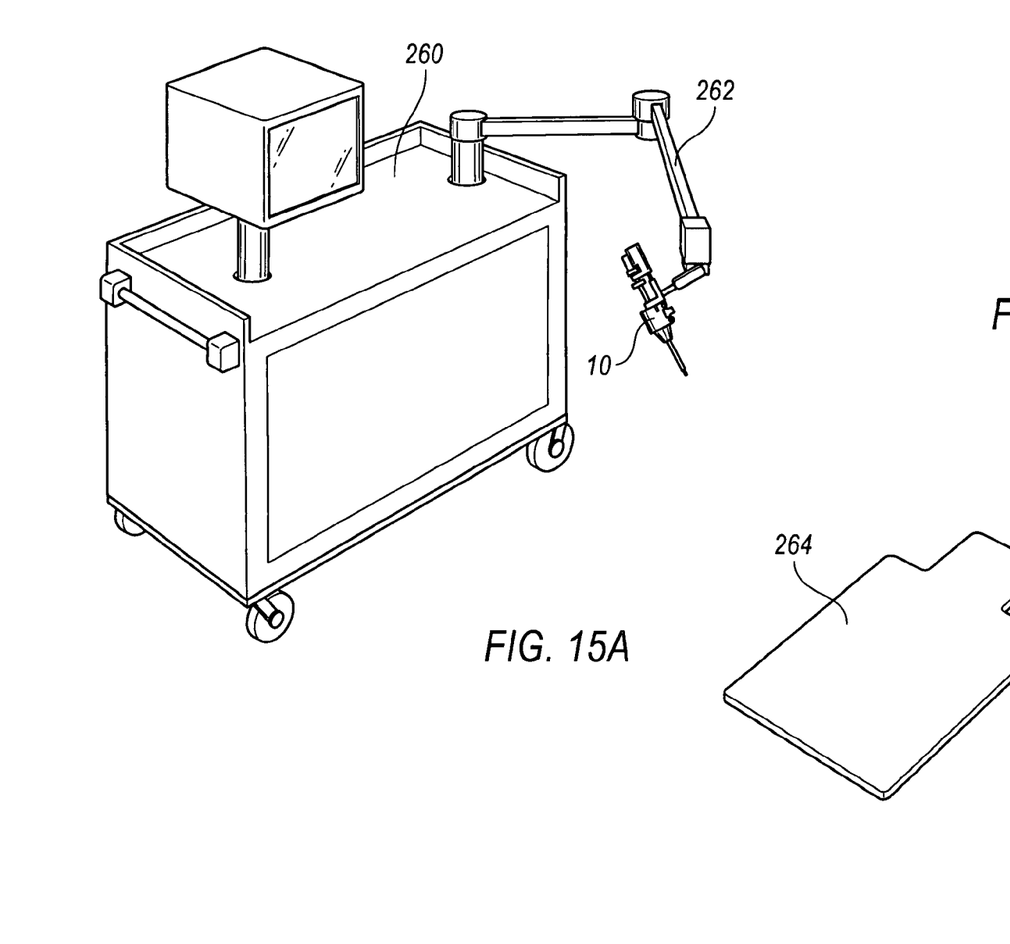
FIG. 15A illustrates a perspective view of a surgical system used in conjunction with a support device relative to an operating table.

FIG. 15A illustrates a perspective view of surgical system 10 used in conjunction with a support device 262 relative to an operating table 264. The surgeon may desire to stabilize surgical system 10 using support device 262 attached to a cart 260. Alternatively, support device 262 may also be a tripod set upon the floor or a fixture designed to rigidly engage the surgical table. Support device 262 may be attached to surgical system 10 by a support receiver integrated with surgical adapter 30, endoscope 44, endoscope adapter 46, extension adjuster 48, introducer body 42, or handpiece 50. The support receiver may be implemented as a threaded receiver or a clamping device that engages surgical system 10 with support device 262. When attached to support device 262, surgical system 10 may be arbitrarily positioned relative to operating table 264.

Figure 15B:
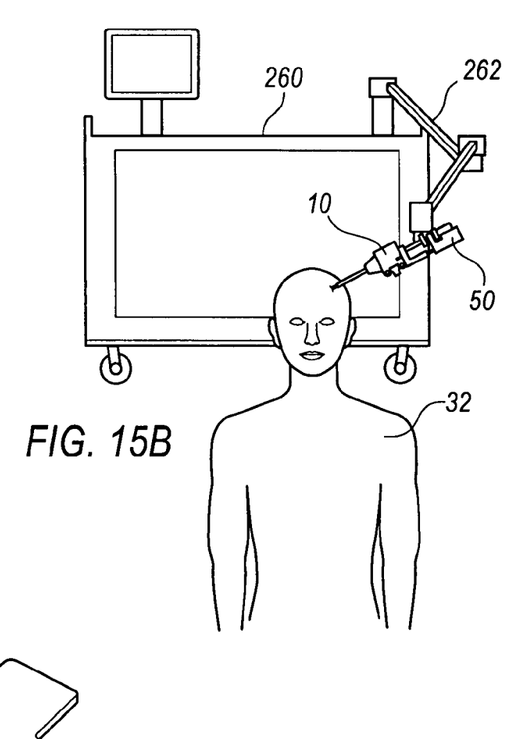
FIG. 15B illustrates a perspective view of a surgical system used in conjunction with a support device wherein the surgical system is positioned relative to a patient.

FIG. 15B illustrates a perspective view of surgical system 10 used in conjunction with support device 262 wherein surgical system 10 is positioned relative to patient 32. Using Support device 262, surgical system 10 is stabilized in the surgical channel and the surgeon is free to conduct the operation without the overhead of holding blade 52 and endoscope 44. Thus, the surgeon is free to rotate blade 52 and adjust the depth of blade 52 without manually stabilizing and positioning surgical system 10.

Accordingly, the present invention facilitates adjustable and fixed positioning of a surgical device within the patient with reduced oversight by the surgeon. The present invention also provides for the removal of the surgical device from working channel 34 and provides for reinsertion of the device to the same prior position. If removal of blade 52 is desired, handpiece 50 is withdrawn proximally away from surgical adapter 30. Blade 52 also withdraws through working channel 34 and can be removed entirely from the system. With the surgical device removed from working channel 34, other devices or therapeutics may be introduced into the patient.

However, blade 52 may be reinserted into working channel 34 until handpiece 50 abuts surgical adapter 30, at which time blade 52 will maintain the original registration with distal end 38, and thus with surgical site 40 (see FIG. 1A), provided that extension adjuster 48 is not disturbed while blade 52 was removed.

Working in combination with axial positioner 220 (illustrated in FIG. 12), the present invention provides the surgeon with complete control of the position and orientation of the cutting mouth, or tissue receiving opening 226, if a cutting instrument is used. Surgical system 10 controls the extension of blade 52 from working channel 34 and optional axial positioner 220 controls the axial position of tissue receiving opening 226 (see FIG. 12). In this way complete registration of tissue receiving opening 226 is maintained. Used in combination with the support (discussed above), the surgeon has complete control over the cutting instrument without having to hold the device.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A surgical system comprising:
   a device body including a working channel providing a pathway for an instrument;
   an extension adjuster engaged with said device body, the extension adjuster having a mounting bracket, a first extension member, and a second extension member;
   wherein the mounting bracket includes a wall member defined by a distal surface and a proximal surface;
   wherein the first extension member is defined by a distal end and a proximal end, the distal end being fixedly connected to the mounting bracket such that the first extension member extends from the mounting bracket in a proximal direction, away from proximal surface of the mounting bracket, the first extension member further comprising a passage extending therethrough;
   wherein the second extension member is defined by a distal end and a proximal end and includes an interior chamber, wherein the proximal end of the second extension member further includes an outer opening that is in communication with the interior chamber;
   wherein the first extension member is received within the interior chamber of the second extension member so as to mate the first and second extension members together such that the second extension member is selectively moveable over the first extension member;
   wherein the second extension member is disposed a predetermined distance from the working channel such that the second extension member and the distal end of the working channel cooperate to define an effective working channel length; and
   whereby the instrument may be inserted through the passage and working channel such that the instrument protrudes outwardly from the distal end of the working channel by a predetermined length, the extent of the protrusion limited by the effective working channel length whereby the second extension member prevents further insertion of the instrument.

2. The system of claim 1, wherein said extension adjuster further includes:
   an abutting surface on the second extension member that may directly engage the instrument, said abutting surface configured to inhibit distal movement of the instrument through the working channel when said abutting surface is engaging the instrument.

3. The system of claim 1, further including a guide system for aligning the instrument with the working channel.

4. The system of claim 3, wherein said guide system further includes:
   at least one first guide element;
   at least one second guide element; and
   such that said at least one first guide element cooperatively engages with said at least one second guide element.

5. The system of claim 4, wherein said at least one first guide element engages said device body.

6. The system of claim 1, wherein:
   said second extension member is engaged with said device body; and
   said first extension member is cooperatively engaged with said second extension member to set the predetermined distance.

7. The system of claim 1, wherein said device body is an endoscope.

8. The system of claim 1, wherein said extension adjuster further comprises at least one fastener for engaging said device body.

9. The system of claim 1, wherein the surgical system further includes a support device, whereby said support device stabilizes the surgical system relative to a surgical site.

10. The system of claim 1, further comprising an extension adapter, which comprises a cavity for receiving said device body.

11. A surgical system for introducing an instrument to a surgical site, said surgical system comprising:
   a device body;
   a working channel extending through and distally away from the device body, the working channel having a distal end for deploying the instrument to the surgical site;
   an extension adapter engaged with the device body; and
   an extension adjuster engaged with the base, the extension adjuster having a mounting bracket, a first extension member, and a second extension member;
   wherein the mounting bracket includes a wall member defined by a distal surface and a proximal surface, the mounting bracket being positioned proximal of the extension adjuster, the mounting bracket engaging the extension adapter;
   wherein the first extension member is defined by a distal end and a proximal end, the distal end being fixedly connected to the mounting bracket such that the first extension member extends from the mounting bracket in a proximal direction, away from proximal surface of the mounting bracket, the first extension member further comprising a passage extending therethrough;
   wherein the second extension member is defined by a distal end and a proximal end and includes an interior chamber, wherein the proximal end of the second extension member further includes an outer opening that is in communication with the interior chamber;

wherein the first extension member is received within the interior chamber of the second extension member so as to mate the first and second extension members together such that the second extension member is selectively moveable with respect to the first extension member;

wherein the second extension member is disposed a predetermined distance from the working channel such that the second extension member and the distal end of the working channel cooperate to define an effective working channel length; and whereby the instrument may be inserted through the passage, the interior chamber and the working channel such that the instrument protrudes outwardly from the distal end of the working channel by a predetermined length, the extent of the protrusion limited by the second extension member, preventing further insertion of the instrument.

12. The system of claim 11, wherein said device body is an endoscope.

13. The system of claim 11, further including:
an abutting surface disposed upon said second extension member;
a mating surface disposed upon the instrument and configured for selectively and directly engaging said abutting surface; and
whereby engagement of said abutting surface and said mating surface inhibits further movement of the instrument toward said device body.

14. The system of claim 11, further including a guide system for aligning the instrument with said working channel, wherein said guide system further includes:
at least one first guide element; and
at least one second guide element cooperatively engaging said at least one first guide element for aligning the instrument with said working channel; wherein said second guide element is formed in a lower portion of the mounting bracket.

15. The system of claim 14, wherein said at least one first guide element engages said device body.

16. The system of claim 11, wherein the surgical system further includes a support receiver for engaging a support device, whereby said support device stabilizes the surgical system relative to a surgical site.

17. The surgical system of claim 11, wherein the second extension member includes a threaded portion disposed within the interior chamber and extending a predetermined distance from the distal end of the second extension member toward the proximal end of the second extension member, the threaded portion cooperating with a corresponding threaded portion disposed on an exterior surface of the first extension member, wherein the corresponding threaded portion extends from the proximal end of the first extension member a predetermined distance toward the distal end of the first extension member.

18. The surgical system of claim 17, wherein the second extension member includes a threaded portion disposed within the interior chamber and extending a predetermined distance from the distal end of the second extension member toward the proximal end of the second extension member, the threaded portion cooperating with a corresponding threaded portion disposed on an exterior surface of the first extension member, wherein the corresponding threaded portion extends from the proximal end of the first extension member a predetermined distance toward the distal end of the first extension member.

* * * * *